United States Patent [19]

Clayton

[11] 4,081,545
[45] Mar. 28, 1978

[54] PENICILLINS

[75] Inventor: John Peter Clayton, Horsham, England

[73] Assignee: Beecham Group Limited, United Kingdom

[21] Appl. No.: 736,897

[22] Filed: Oct. 29, 1976

[30] Foreign Application Priority Data

| Oct. 31, 1975 | United Kingdom | 45214/75 |
| Jan. 20, 1976 | United Kingdom | 2072/76 |
| Apr. 28, 1976 | United Kingdom | 21514/76 |

[51] Int. Cl.$^2$ .................. A61K 31/43; C07D 499/64; C07D 499/68; C07D 499/70
[52] U.S. Cl. .................. 424/271; 260/239.1
[58] Field of Search .................. 260/239.1; 424/271

[56] References Cited

U.S. PATENT DOCUMENTS

| 3,433,784 | 3/1969 | Long et al. | 260/239.1 |
| 3,939,150 | 2/1976 | Murakami et al. | 260/239.1 |
| 3,945,995 | 3/1976 | Yamada et al. | 260/239.1 |
| 3,953,428 | 4/1976 | Murakami et al. | 260/239.1 |
| 3,954,733 | 5/1976 | Tobiki et al. | 260/239.1 |

Primary Examiner—Gerald A. Schwartz
Attorney, Agent, or Firm—Jacobs & Jacobs

[57] ABSTRACT

A class of α-(heterocyclic carbonylamino) penicillins in which the heterocyclic group of the acyl moiety is a fused bicyclic ring having a nitrogen atom at the bridge position, shows good antibacterial activity.

33 Claims, No Drawings

PENICILLINS

This invention relates to penicillin antibiotics and in particular to a class of α-(heterocyclic carbonylamino) penicillins.

The heterocyclic group of the acyl moiety is characterised by being a fused bicyclic ring system having a nitrogen atom at the bridge position.

According to one embodiment of the present invention there is provided a penicillin derivative of formula (I) or a pharmaceutically acceptable non-toxic salt or in vivo hydrolysable ester thereof:

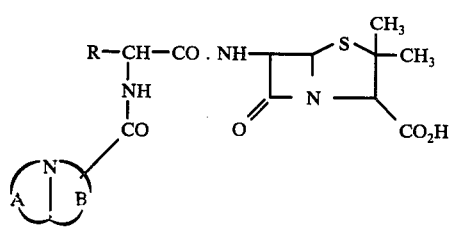

wherein R represents a furyl, thienyl, cycloalkyl, cycloalkenyl or phenyl group, or a phenyl group substituted by hydroxy, halogen, nitro, lower alkyl, lower alkoxy, amino, or carboxy; and A and B are the same or different and each represents the residue of a fused 5- or 6- membered ring.

The compounds of the present invention include the pharmaceutically acceptable non-toxic esters of compound (I). Suitable esters include those which hydrolyse readily in the human body to produce the parent acid, for example alkoxyalkyl esters such as methoxymethyl esters, acyloxyalkyl esters such as acetoxymethyl, pivaloyloxymethyl, α-acetoxyethyl, α-acetoxybenzyl and α-pivaloyloxyethyl esters; alkoxycarbonyloxyalkyl esters, such as ethoxycarbonyloxymethyl and α-ethoxycarbonyloxyethyl; and lactone, thiolactone and dithiolactone esters, i.e. ester groups of formula:

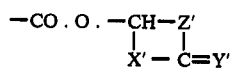

wherein X' and Y' are oxygen or sulphur and Z' is an ethylene group or a 1,2-phenylene group optionally substituted by lower-alkoxy, halogen or nitro.

Preferred ester groups are the phthalide and 3,4-dimethoxyphthalide esters.

Suitable salts of the compound of formula (I) include metal salts, e.g. aluminium, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amine,tris(hydroxymethyl)amine or tris-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with benzylpenicillin.

Pharmaceutically acceptable acid addition salts of such a compound are also included within this invention. Suitable acid addition salts of the compounds of formula (I) include, for example inorganic salts such as the sulphate, nitrate, phosphate, and borate; hydrohalides e.g. hydrochloride, hydrobromide and hydroiodide; and organic acid addition salts such as acetate, oxalate, tartrate, maleate, citrate, succinate, benzoate, ascorbate, methanesulphonate and p-toluenesulphonate, trifluoroacetate.

Suitable groups R in the compounds of formula (I) include 2- and 3- furyl, 2- and 3- thienyl, cyclopropyl, cyclobutyl, cyclopentyl, cyclohexyl, cyclobutenyl, cyclopentenyl, cyclohexenyl, cyclohexa-1,4-dienyl, phenyl, 4-hydroxyphenyl, 3-chloro-4-hydroxyphenyl, 3,4-dihydroxyphenyl. Suitably R is a 2- or 3-thienyl, phenyl or 4-hydroxyphenyl group; preferably R is phenyl or 4-hydroxyphenyl.

In the structure (I) above, A and B are each defined as a residue of a 5- or 6- membered ring. Such rings may be either saturated or unsaturated and may contain further hetero atoms such as nitrogen, sulphur, or oxygen. The rings may be unsubstituted or substituted with lower alkyl, for example methyl, ethyl, n- and iso-propyl, butyl; lower alkoxy, for example methoxy, ethoxy, n- and iso-propoxy, butoxy; lower-alkoxycarbonyl, for example methoxycarbonyl, ethoxycarbonyl, propoxycarbonyl; hydroxyl; halogen, for example chlorine, bromine, iodine, fluorine; halo(lower)alkyl for example chloromethyl, trifluoromethyl; nitro; oxo; loweralkylsulphonyl for example methanesulphonyl; mercapto; lower alkylthio, for example methylthio, ethylthio, propylthio; amino; loweralkylamino, for example methylamino, ethylamino, propylamino; di(lower)alkylamino, for example dimethylamino, diethylamino, methylethylamino; lower-alkoxycarbonyloxy for example methoxy-carbonyloxy, ethoxycarbonyloxy; lower-alkoxycarbonylthio, for example methoxycarbonylthio, ethoxycarbonylthio. Alternatively, two substituents on ring A may be joined to form a further fused ring, preferably a benzene ring optionally substituted with any of the above substituents. Preferred substituents include lower alkyl, lower alkoxy, halogen and amino.

In this specification the prefix 'lower' is intended to mean a group having from 1 to 6 carbon atoms.

One class of compounds within the present invention are those having the formula (II) or a pharmaceutically acceptable non-toxic salt or ester thereof:

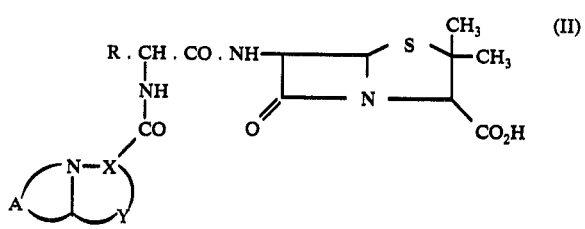

wherein R and A are as defined with respect to formula (I) above; X represents a group of formula:

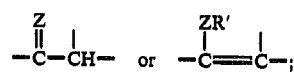

in which Z represents oxygen or sulphur; R' represents hydrogen, lower alkyl or lower alkoxycarbonyl; Y represents the residue of a fused 5- or 6- membered saturated or unsaturated ring. Preferably Z is oxygen and R' is hydrogen.

The fused bicyclic moeity of formula (II) may have one of the following structures (A) - (F):

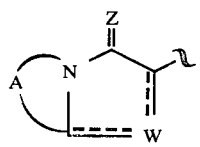
(A)

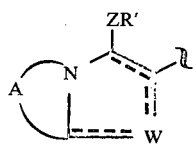
(B)

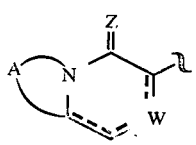
(C)

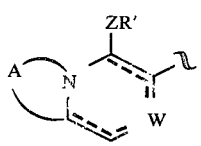
(D)

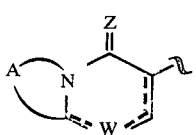
(E)

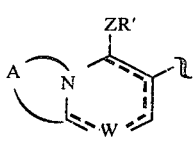
(F)

wherein the dotted lines represent optional double bonds in one or two of the positions shown; and when one bond from the group W is a double bond, then W is a nitrogen atom or a —CH— group and when both bonds from the group W are single bonds, then W is an oxygen or sulphur atom or a $CH_2$ or $NR^2$ group, wherein $R^2$ is hydrogen or lower alkyl; and A,Z and R' are as defined with respect to formula (II) above. Preferred structures are (E) and (F) above, and W is nitrogen, or sulphur, especially when W is nitrogen.

The radical A may suitably complete a 5- or 6-membered ring containing from one to four nitrogen atoms and from zero to two oxygen or sulphur atoms. Suitable rings which the radical A completes include pyrazine, pyridine, thiazoline, triazine, thiazolidine, tetrahydropyridine, tetrazole, pyrazole, triazole or oxazole. Preferably A completes a 5-membered ring; especially pyrazole or triazole.

Suitable classes of fused bicyclic systems in formula (II) include the following structures types G, H & J, which may be unsubstituted or substituted:

(G) [4,4,0]systems containing one nitrogen, such as:

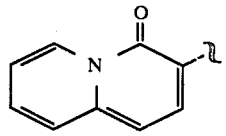

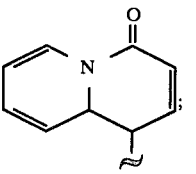

or two nitrogens, such as:

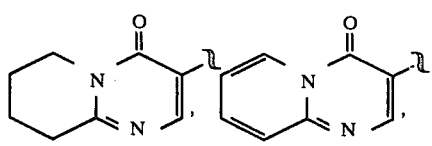

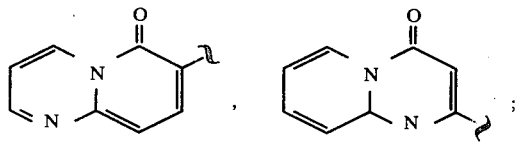

or three nitrogens, such as:

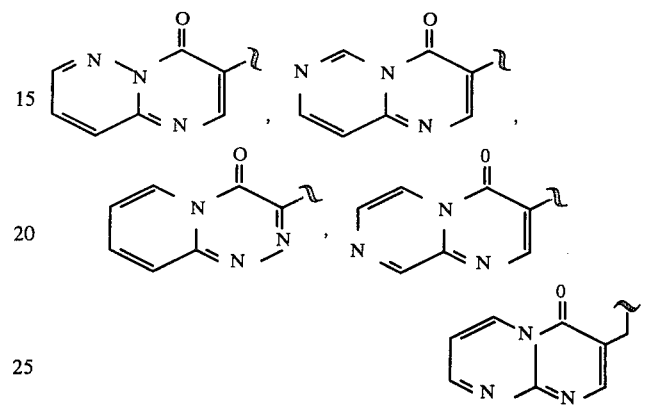

(H) [4,3,0] systems containing one nitrogen, such as:

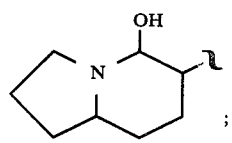

or two nitrogens, such as:

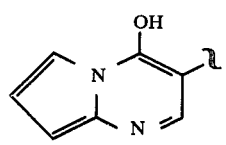

or three nitrogens, such as:

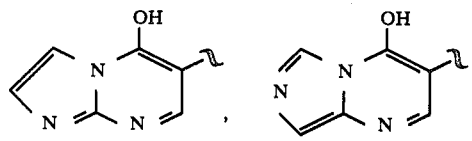

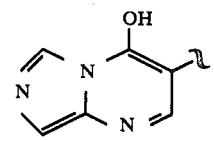

or four nitrogens, such as:

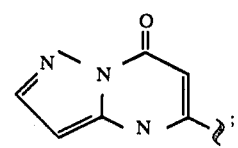

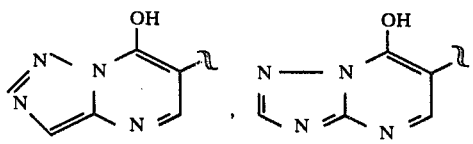

or five nitrogens, such as:

(J) [4,3,0] oxo or thio systems, such as:

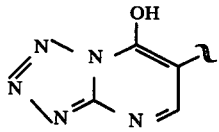

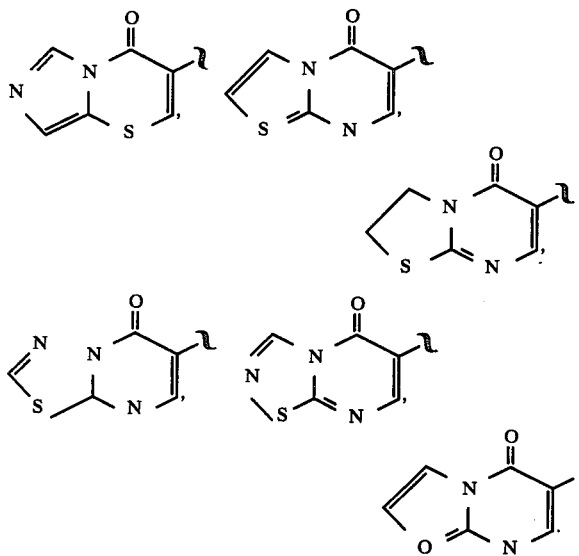

Specific examples of bicyclic moieties of the type (G) include the following, and tautomers thereof:
pyridotriazines:

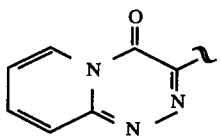

for example
D,α-(4-oxo-4H-pyrido[2,1-c]as-triazine-3-carbonylamino)benzyl penicillin;
pyridopyrimidines:

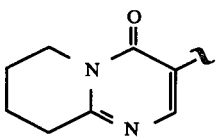

for example, 6-D-[2-(4-oxo-4H-pyrido[1,2-a]-pyrimidine-3-carboxamido)-2-phenylacetamido]penicillanic acid; 6-R-[R-2-(6,7,8,9-tetrahydro-4-oxo-4H-pyrido-[1,2-a]pyrimidine-3-carboxamido)-2-phenylacetamido]-penicillanic acid. Examples of bicyclic moieties of type (H) include the following and tautomers thereof:
triazolopyrimidines:

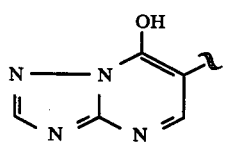

for example,

6-D-[2-(7-hydroxy-1,2,4-triazolo[1,5-a]pyrimidine-6-carboxamido)-2-phenylacetamido]penicillanic acid; 6-D-[2-(7-hydroxy-1,2,4-triazolo[1,5-a]pyrimidine-6-carboxamido)-2-p-hydroxyphenylacetamido]penicillanic acid; D-α-(3,7-dihydro-3-amino-2-methyl-7-oxo-s-triazolo[1,5-a]-pyrimidine-6-carbonylamino)-benzyl penicillin; and D-α-(4,7-dihydro-4-ethyl-7-oxo-1,2,4-triazolo[1,5-a]-pyrimidine-6-carbonylamino)-p-hydroxybenzyl penicillin;

pyrazopyrimidines:

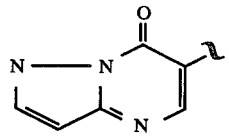

for example,
6-D-[2-(4,7-dihydro-4-ethyl-7-oxo-pyrazolo[1,5-a]pyrimidine-6-carboxamido)-2-phenylacetamido]-penicillanic acid;
6-D-[2-(7-hydroxypyrazolo[1,5-a]pyrimidine-6-carboxamido)-2-phenylacetamido]penicillanic acid;
6-D-[2-(4,7-dihydro-4-ethyl-7-oxo-pyrazolo[1,5-a]pyrimidine-6-carboxamido)-2-p-hydroxyphenylacetamido]penicillanic acid; and
6-D-[2-(7-hydroxypyrazolo[1,5-a]pyrimidine-6-carboxamido)-2-p-hydroxyphenylacetamido]penicillanic acid.

tetrazolopyrimidines:

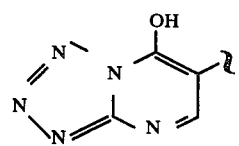

for example, D-α-(7-hydroxy-tetrazolo[1,5-a]pyrimidine-3-carbonylamino)benzyl-penicillin. Examples of bicyclic moeities of the type (J) above include:
thiazolopyrimidines:

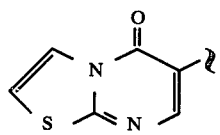

for example,
6-D-[2-(5-oxo-5H-thiazolo[3,2-a]pyrimidine-6-carboxamido)-2-phenylacetamido]penicillanic acid;
6-D-[2-(5-oxo-5H-thiazolo[3,2-a]pyrimidine-6-carboxamido)-2-p-hydroxyphenylacetamido]penicillanic acid;
D-α-(8-methoxy-4-oxo-4H-pyrimido[2,1-b]benzothiazol-3-carbonylamino)benzyl penicillin; and
D,α-(8-methoxy-4-oxo-4H-pyrimido[2,1-b]benzothiazol-3-carbonylamino)-p-hydroxybenzyl penicillin;
oxazolopyrimidines:

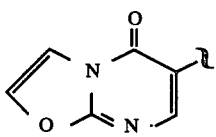

for example
D,α-(7-chloro-4-oxo-4H-pyrimido[2,1-b]benzoxazole-3-carbonylamino)benzyl penicillin;
thiazolidinopyrimidines:

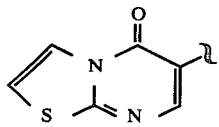

for example,
D,α-(5-oxo-5H-thiazolidino[3,2-a]pyrimidin-6-carbonylamino)benzyl penicillin; and
D,α-(5-oxo5H-thiazolidino[3,2-a]pyrimidin-6-carbonylamino)-p-hydroxybenzyl penicillin.
triazolothiazines:

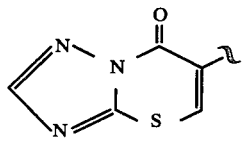

for example, D-α-[7-oxo-7H-1,2,4-triazolo(1,5-b)[1,3]thiazine-6-carboxylamino]benzyl penicillin.

The compounds of formula (I) may be prepared by reacting a compound of formula (III) or an N-protected derivative thereof:

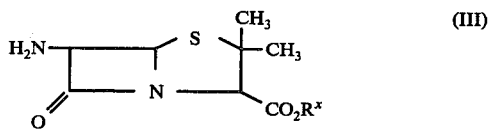

wherein $R^x$ is hydrogen, an in vivo hydrolysable ester radical or a carboxyl blocking group; with an N-acylating derivative of an acid of formula (IV):

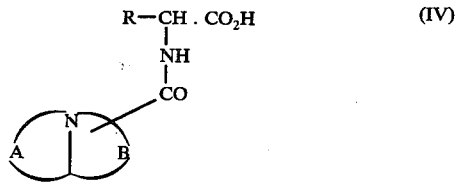

wherein R, A, and B are as defined with respect to formula (I) above and wherein any reactive groups such as amino and hydroxy groups may be blocked; and thereafter if necessary carrying out one or more of the following steps:
(i) removal of any N-protecting groups by hydrolysis or alcoholysis;
(ii) removal of any carboxyl blocking groups;
(iii) removal of any blocking groups in the acyl side chain;
(iv) converting the product to a salt or ester thereof.

Examples of "N-protected derivatives" of compound (III) include N-silyl and N-phosphorylated derivatives.

By the term "N-silyl derivative" of compound (III), we mean the product of reaction of the 6-amino group of compound (III) with a silylating agent such as a halosilane or a silazane of the formula:

$L_3$ Si U; $L_2$ Si $U_2$; $L_3$ Si $NL_2$;

-continued
$L_3$ Si NH Si $L_3$; $L_3$ Si . NH . CO . $L_3$ Si . NH . CO . NH . Si $L_3$;
L NH . CO . NH . Si $L_3$; LC . OSi $L_3$.
NSiL$_3$ wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The term "N-phosphorylated" derivative of compound (III) is intended to include compounds wherein the 6-amino group of formula (IV) is substituted with a group of formula:

$$- P.R_a R_b$$

wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen, or $R_a$ and $R_b$ together form a ring.

Suitable carboxyl-blocking derivatives for the group —$CO_2R^x$ in formula (III) include salts, ester, and anhydride derivatives of the carboxylic acid. The derivative is preferably one which may readily be cleaved at a later stage of the reaction. Suitable salts include tertiary amine salts, such as those with tri-loweralkylamines, N-ethylpiperidine, 2,6-lutidine, pyridine, N-methylpyrrolidine, dimethylpiperazine. A preferred salt is with triethylamine.

Suitable ester groups of formula —$CO_2R^x$ include the following:
(i) —$COOCR_cR_dR_e$ wherein at least one of $R_c$, $R_d$, and $R_e$ is an electron-donor e.g. p-methoxyphenyl, 2,4,6-trimethylphenyl, 9-anthryl, methoxy, acetoxy, or fur-2-yl. The remaining $R_c$, $R_d$ and $R_e$ groups may be hydrogen or organic substituting groups. Suitable ester groups of this type include p-methoxybenzyloxycarbonyl, 2,4,6-trimethylbenzyloxy carbonyl, bis(p-methoxyphenyl)methoxycarbonyl, and 3,5-di-t-butyl-4-hydroxybenzyloxycarbonyl.
(ii) —$COOCR_cR_dR_e$ wherein at least one of $R_c$, $R_d$, and $R_e$ is an electron-attracting group e.g. benzoyl, p-nitrophenyl, 4-pyridyl, trichloromethyl, tribromomethyl iodomethyl, cyanomethyl, ethoxycarbonylmethyl, arylsulphonylmethyl, 2-dimethylsulphoniumethyl, o-nitrophenyl or cyano. The remaining $R_c$, $R_d$, and $R_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.
(iii) —$COOCR_cR_dR_e$ wherein at least two or $R_c$, $R_d$, and $R_e$ hydrocarbon such as alkyl e.g. methyl or ethyl, or aryl e.g. phenyl and the remaining $R_c$, $R_d$, and $R_e$ group if there is one, is hydrogen. Suitable esters of this type include t-butyloxycarbonyl, t-amyloxycarbonyl, diphenylmethoxycarbonyl and triphenylmethoxycarbonyl.
(iv) —$COOR_f$ wherein $R_f$ is adamantyl, 2-benzyloxyphenyl, 4-methylthiophenyl, tetrahydrofur-2-yl, tetrahydropyran-2-yl, pentachlorophenyl.
(v) Silyloxycarbonyl groups obtained by reaction of a silating agent as described above with the carboxylic acid group.

(vi) $CO_2P.R_aR_b$, wherein $R_a$ and $R_b$ are as defined above.

(vii) trialkyltin esters.

(viii) oxime esters of formula $CO_2N=CH.R_g$ where $R_g$ is aryl or heterocyclic.

The carboxyl group may be regenerated from any of the above esters by usual methods appropriate to the particular $R^x$ group, for example, acid — and base — catalysed hydrolysis, or by enzymically — catalysed hydrolysis. Alternative methods of cleavage include:

reaction with Lewis acids, such as trifluoroacetic acid, formic acid, hydrochloric acid in acetic acid zinc bromide in benzene and aqueous solutions or suspensions of mercuric compounds. (The reaction with the Lewis acid may be facilitated by addition of a nucleophile such as anisole);

reduction with agents such as zinc/aqueous acetic acid, zinc/formic acid, zinc/lower alcohol, zinc/pyridine, or hydrogen and palladised-charcoal or other supported hydrogenation catalysts.

attack by nucleophiles, such as those containing a nucleophilic oxygen or sulphur atom for example alcohols, mercaptans and water; oxidative methods, for example, those which involve the use of hydrogen peroxide and acetic acid; and irradiation with light or U.V.

A reactive N-acylating derivative of the acid (IV) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{2-6})$-1,2-alkylene oxide-such as ethylene oxide or propylene oxide. The acylation reaction using an acid halide may be carried out at a temperature in the range $-50°$ to $+50°$ C, preferably $-20°$ to $+30°$ C, in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water- immiscible solvent, especially an aliphatic ester of ketone, such as methyl isobutyl ketone or butyl acetate.

The acid halide may be prepared by reacting the acid (IV) or a salt thereof with a halogenating (e.g. chlorinating or brominating) agent such as phosphorus pentachloride, thionyl chloride or oxalyl chloride.

Alternatively, the N-acylating derivative of the acid (IV) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst. Another type of anhydride is the 2,5-oxazolidinedione of formula (V):

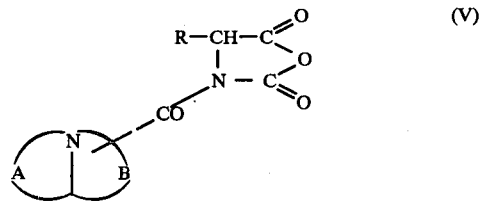

wherein R, A, and B are as defined with respect to formula (I) above. Compound (V) may be prepared from the acid (IV) by the action of phosgene.

Alternative N-acylating derivatives of acid (IV) are the acid azide, or activated esters such as esters with 2-mercaptopyridine, cyanomethanol, p-nitrophenol, 2,4-dinitrophenol, thiophenol, halophenol, including pentachlorophenol, monomethoxyphenol or 8-hydroxyquinoline; or amides such as N-acylsaccharins or N-acylphthalimides; or an alkylidene iminoester prepared by reaction of the acid (IV) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (IV) include the reactive intermediate formed by reaction in situ with a condensing agent such as carbodiimide, for example, N,N-diethyl-, dipropyl- or diisopropylcarbodiimide, N,N'-cyclohexylcarbodiimide, or N-ethyl-N'-γ-dimethylaminopropylcarbodiimide; a suitable carbonyl compound, for example, N,N'-carbonyldiimidazole or N,N'-carbonylditriazole; and isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3 — C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

With the above route it is preferable to protect any reactive groups in the acyl side-chain prior to the acylation reaction. When the group to be protected is an amino group, any of the amino groups known from the literature on the synthesis of α-aminobenzyl penicillin are suitable.

Compounds of formula (I) may also be prepared by reacting a compound of formula (VI):

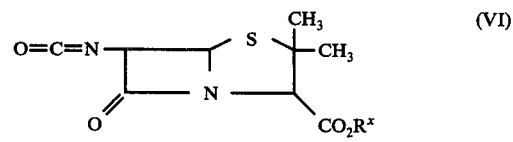

wherein $R^x$ is as defined with respect to formula (III) above; with an acid of formula (IV) wherein any reactive groups may be blocked; and thereafter if necessary carrying out one or more of the following steps:

(i) removal of any carboxyl blocking group;
(ii) removal of any blocking groups in the acyl side chain;
(iii) converting the product to a salt or ester thereof.

This reaction is preferably carried out at a temperature in the range −10° to +50° C in an inert organic solvent, such as methylene dichloride, in the presence of a basic catalyst such as triethylamine, pyridine or a nitrogen-containing aromatic mono- or bi-cyclic compound such as 4-methoxy(dimethylamino)-pyridine, 1-methyl(benz)imidazole or imidazo [1,2-a]pyridine.

A third method of preparation of the compounds of formula (I) comprises:

(a) protecting the 3-carboxylic acid group of a 6-acylamino penicillanic acid with a carboxyl blocking group;

(b) reacting the protected penicillanic acid to form an imino bond on the 6-amido nitrogen atom;

(c) reacting the resulting compound to introduce a group QR$_f$ on the imino carbon atom, wherein Q is oxygen, sulphur or nitrogen and R$_f$ is an alkyl group of from 1 to 12 carbon atoms or an aralkyl group of from 5 to 14 carbon atoms, to form an iminoether, iminothioether or amidine (when Q is O, S or N respectively);

(d) reacting with an acylating derivative of an acid of formula (IV) above;

(e) treating with water or an alcohol; and (f) thereafter if necessary carrying out one or more of the following steps:

(i) removal of any carboxyl blocking groups;

(ii) removal of any blocking groups in the acyl side chain;

(iii) converting the product to a salt or ester thereof.

In the above process, after protection of the 3-carboxylic acid group, the protected penicillanic acid is reacted with an agent to form an imino bond on the 6-amido nitrogen atom. Preferably an imino halide is formed of formula (VII):

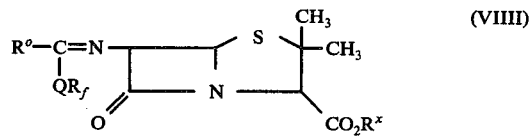

(VII)

wherein R$^o$ is the residue of an organic acylamino sidechain of a penicillin, R$^x$ is a carboxyl blocking group and Hal represents a halogen atom. A suitable agent for preparing an imino halide is an acid halide in the presence of an acid binding agent such as tertiary amine, e.g. pyridine, triethylamine, or N,N-dimethylaniline. Examples of suitable acid halides are phosphorus pentachloride, phosgene, phosphorus pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from 0° C to −30° C when phosphorus pentachloride is employed. The amount of the tertiary amine is preferably 3-5 mols per mol of phosphorus pentachloride. It is also preferable to use the phosphorus halide in an amount slightly in excess of that of the starting material.

The resulting imino compounds are then treated to introduce a −QR$_f$ grouping, onto the imino carbon atom, to produce a compound of formula (VIII):

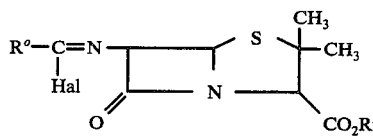

(VIII)

wherein R$^o$, Q, R$_f$ and R$^x$ are as defined above.

This is preferably effected by reacting an imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenyl-ethanol-1. The reaction of the alcohol with the imino halide is preferably effected in the presence of an acid binding agent, such as a tertiary amine, preferably pyridine, and the reaction is usually carried out without isolating the imino halide from the reaction mixture.

Thereafter the compound (VIII) is caused to react with an N-acylating derivative of an acid of formula (IV). The comments made above concerning such N-acylating derivative, and the conditions for carrying out acylations also apply in this case. In particular the presence of a tertiary amine such as pyridine or N,N-dimethylaniline in the reaction system is preferred. The product from such an acylation has formula (IX):

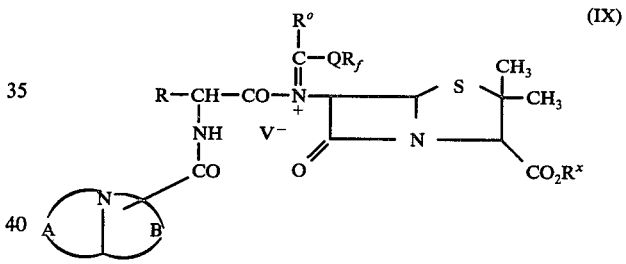

Finally, the addition compound (IX) is treated with water or alcohol. The water treatment may be conducted together with the isolation of the desired material. That is, water or a saturated aqueous solution of sodium chloride is added to the compound (IX) and then the aqueous layer formed is separated from the organic solvent layer.

Alternatively a compound of formula (IXA):

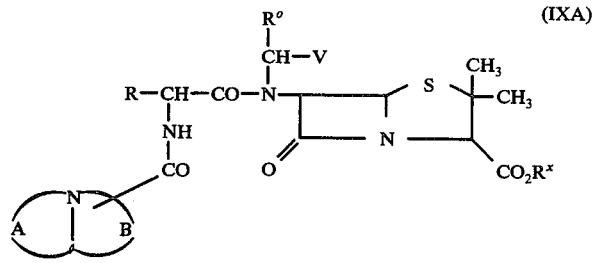

wherein R, R$^o$, R$^x$, A and B are as defined above and V is the residue of an N-acylating derivative of the acid (IV), (e.g. hydroxy, halogen, acyloxy, aryloxy, amino, cyano, azido); may be prepared by reaction of the corresponding N-acylating derivative of (IV) with the Schiff's base formed by reacting 6-aminopenicillanic acid (or a carboxyl protected derivative thereof) with an aldehyde R⁰.CHO. The compound (IXA) may be hydrolysed to a compound (I) with water optionally in the presence of acid or base.

A further method for the preparation of compounds of formula (I) is by hydrolysis or aminolysis of an N-acylbenzylpenicillin of formula (X):

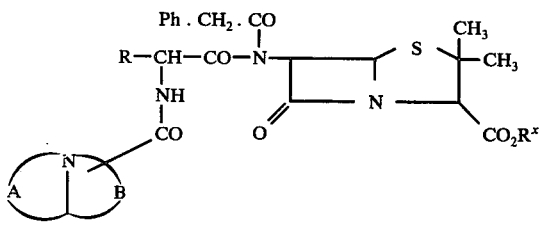

wherein R, R$^x$, A and B are as defined above. The hydrolysis may be an acid- or base-catalysed chemical hydrolysis or may be an enzymic hydrolysis with the aid of penicillin acylase. The compound (X) may be prepared either from an imino-halide compound of formula (VII) above the reaction with a salt of the acid (IV); or by the action of an acid halide of the acid (IV) with a 6-N-alkali metal derivative of benzylpenicillin.

The compounds of formula (I) may also be prepared by reaction of a compound of formula (XI) or an N-protected derivative thereof:

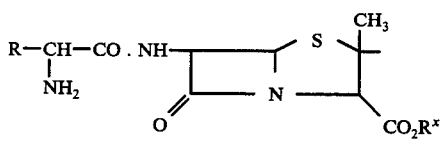

wherein R is as defined with respect to formula (I) and R$^x$ is a carboxyl blocking group; with an N-acylating derivative of an acid of formula (XII):

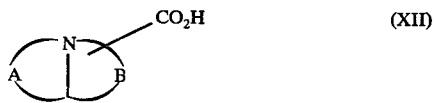

(XII)

wherein A and B are as defined with respect to formula (I) above and wherein any reactive groups such as amino and hydroxy groups may be blocked; and thereafter if necessary carrying out one or more of the following steps:

(i) removal of any N-protecting groups by hydrolysis or alcoholysis;

(ii) removal of any carboxyl blocking groups;

(iii) removal of any blocking groups in the acyl side chain;

(iv) converting the product to a salt or ester thereof.

The comments made earlier concerning N-protected derivatives, blocking groups and N-acylating derivatives also apply to this process.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the aceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel of hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg., of the active ingredient. The dosage as employed for adult human treatment will preferably range from 100 to 3000 mg., per day, for instance 1500 mg., per day, depending on the route and frequency of administration.

The compound of formula (I) may be the sole therapeutic agent in the compositions of the invention or a combination with other antibiotics may be employed. Advantageously the compositions also comprise a compound of formula (XIII) or a pharmaceutically acceptable salt or ester thereof;

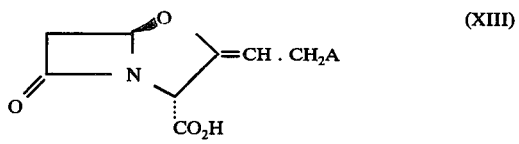
(XIII)

wherein A is hydrogen or hydroxyl.

Preferably the compound of formula (XIII) is clavulanic acid of formula (XIV) or a pharmaceutically acceptable salt or ester thereof:

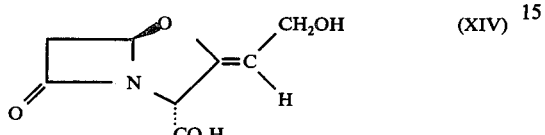
(XIV)

The preparation of these compounds is described in Belgium Pat. Nos. 827,926, 836,652 and West German Offenlegungsschrift no. 2,616,088.

It will be clear that the side-chain of the penicillins of formula (I) contains a potentially asymmetric carbon atom. This invention includes all the possible epimers of compounds (I) as well as mixtures of them.

The following Examples illustrate the preparation of some of the compounds of this invention.

In the Examples, the following publications are referred to:
1. G. L. Lappin JACS 70, 3348 (1948).
2. R. Adams and I. J. Pachter JACS 74, 5491, (1952).
3. Y. Makisumo Chem. Pharm. Cull, 10, 620, (1962).
4. K. Senga et. al. J. Med. Chem. 18, 313, (1975).

EXAMPLE 1

6-D-[2-(4-Oxo-4H-pyrido[1,2-a]pyrimidine-3-carboxamido)-2-phenylacetamido]penicillanic acid (a) Diethyl 2-pyridylaminomethylenemalonate[1]

A mixture of 2-aminopyridine (2.5g., 27mM) and diethyl ethoxymethylenemalonate (7.5g., 70mM) was heated in an open flask at 110° C for one hour and 180° C for ¾ hour. The reaction mixture was cooled, diluted with ethanol (15 ml) and cooled in ice. The precipitate was filtered off and recrystallised from ethanol to give a white product. Yield 4.36g., (61.2%). m.p. 62°–68° C. Thin layer chromatography showed one component at $R_f$ 0.77 (chloroform/acetone/acetic acid; 50:50:7). $\delta$ (CDCl$_3$) 11.20 (1H, d, NH), 9.31 (1H, d, NHC$\underline{H}$=), 8.7–6.9 (4H, m, H),

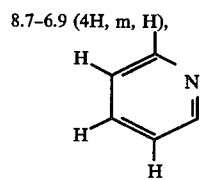

4.33 (4H, m, —COOC$\underline{H}_2$CH$_3$), 1.37 (6H, m, — CO$_2$CH$_2$C$\underline{H}_3$); νmax (nujol) 1670 (C=O), 1640 (C=C) cm$^{-1}$; λmax (MeOH) 277 (εm, 9,640) 324 (εm 31,600)nm. (Found: C, 58.84; H, 6.28; N, 10.54%. C$_{13}$H$_{16}$N$_2$O$_4$ requires C, 59.1; H, 6.1; N, 10.6%), (b) Ethyl 4-oxo-4H-pyrido[1,2-a]pyrimidine-3-carboxylate[2]

To refluxing diphenyl ether (20 ml), was added diethyl 2-pyridylaminomethylenemalonate (2g). The resulting solution was heated under reflux for 20 minutes, cooled and diluted with 40°/60° petroleum ether (100 ml). The yellow precipitate was filtered off and dried in vacuo Yield 611mg (40%). m.p. 98°–99° C. Thin layer chromatography showed one component at Rf 0.55 (Chloroform/acetone/acetic acid; 50:50:7). ε (CDCl$_3$), 9.4 (1H, d, H) 9.12   (1H, s, O),

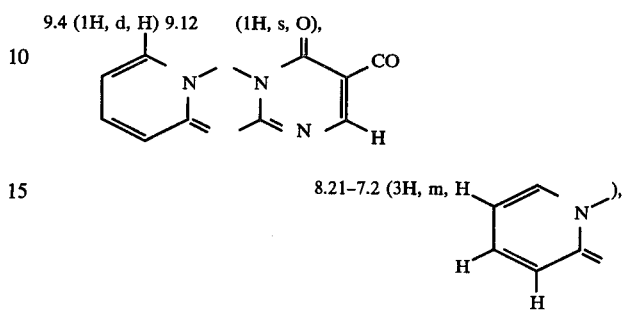

8.21–7.2 (3H, m, H 4.5 (2H, q, —COOC$\underline{H}_2$CH$_3$), 1.42 (3H t, — COOCH$_2$C$\underline{H}_3$); μmax (nujol) 1730 (C=O)cm$^{-1}$. The organic extract was washed with water and was then extracted with 0.1N sodium bicarbonate solution (2 × 10ml). This sodium bicarbonate extract was washed with ethyl acetate (2 × 25ml) and then covered with ethyl acetate (50 ml) and acidified to pH 3.0 with 1N hydrochloric acid. The ethyl acetate extract was washed with water, brine, dried over magnesium sulphate, filtered and evaporated to dryness. The required product was obtained in 57.6% weight yield (300 mg). Thin layer chromatography/chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf = 0.38. ε (DMSO-d$^6$), 10.18 (1H, d, NH); 9.58 (1H, d, NH), 9.41 (1H, d, H), 9.17 (1H, s,    8.6–7.6 (3H,

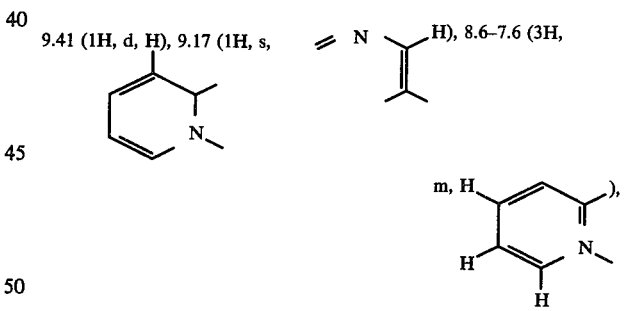

m, H 7.50 (5H, m, Ph—), 6.12 (1H, d α-CH), 5.60 (2H, m, β-lactam), 4.34 (1H, s, H$_3$), 1.65 (3H, s —CH$_3$), 1.50 (3H, s, —CH$_3$); νmax (nujol) 1775 (β-lactam C=O)cm$^{-1}$.

(c) / 4-Oxo-4H-pyrido[1,2-a]pyrimidine-3-carboxylic acid[2]

To 1% sodium hydroxide solution (20ml) at 0°–5° C was added ethyl 4-oxo-4H-pyrido[1,2-a]pyrimidine-3-carboxylate (500mg) with stirring. Stirring was continued at 0°–5° C until solution was complete (1 hour). Glacial acetic acid (0.2 ml) was added to the solution and a white precipitate formed which was filtered and recrystallised from boiling water. The product was dried in vacuo over P$_2$O$_5$. Yield 210 mg (48%). m.p. 248° C (decomposition). Thin layer chromatography showed one component at R$_f$ 0.3 (chloroform/acetone/acetic acid; 50:50:7). ε (DMSO-d$^6$), 9.41 (1H, d, H), 9.17 (1H, s, 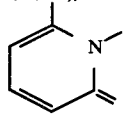), 8.6-7.7 (3H, m, 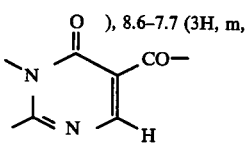); 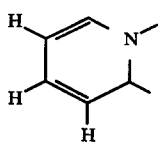

νmax (nujol) 1740, 1730 (C=O)cm$^{-1}$.

(d) 6-D-[2-(4-Oxo-4H-pyrido[1,2-a]pyrimidine-3-carboxamido)2-phenylacetamido]penicillanic acid A solution of 4-oxo-4H-pyrido[1,2-a]pyrimidine-3-carboxylic acid (190 mg., 1mM) in dry distilled N,N-dimethylacetamide (4ml) with triethylamine (0.41ml, 1mM) was cooled to −10° C and treated with isobutyl chloroformate (0.13ml, 1mM). The reaction mixture was stirred at this temperature for a further ½ hour, then treated with a chilled solution of ampicillin trihydrate (403 mg, 1mM) in 0.5N sodium hydroxide solution (2ml). The stirred solution was allowed to reach room temperature (ca 1 hour) and was then poured into water (100ml), covered with ethyl acetate (50ml) and the pH was adjusted to 2.5 with 1N hydrochloric acid.

The organic extract was washed with water and was then extracted with 0.1N sodium bicarbonate solution (2 × 10ml). This sodium bicarbonate extract was washed with ethyl acetate (2 × 25ml) and then covered with ethyl acetate (50ml) and acidified to pH 3.0 with 1N hydrochloric acid. The ethyl acetate extract was washed with water, brine, dried over magnesium sulphate, filtered and evaporated to dryness. The required product was obtained in 57.6% weight yield (300mg). Thin layer chromatography (chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf = 0.38. ε (DMSO-d$^6$), 10.18 (1H, d, NH), 9.58 (1H, d, NH), 9.41 (1H, d, H), 9.17 (1H, s, 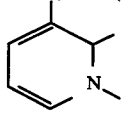), 8.6-7.6 (3H, m, H, 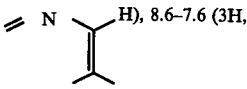), 7.50 (5H, m, Ph-), 6.12 (1H, d, α-CH), 5.60 (2H, m, β-lactam), 4.34 (1H, s, H$_3$), 1.65 (3H, s, —CH$_3$) 1.50 (3H, s, —CH$_3$); νmax (nujol) 1775 (β-lactam C=O)cm$^{-1}$.

EXAMPLE 2

6-D-[2-(4,7-Dihydro-4-ethyl-7-oxo-pyrazolo[1,5-a]pyrimidine-6-carboxamido)-2-phenylacetamido]penicillanic acid (a) Ethyl 7-hydroxypyrazolo[1,5-a]pyrimidine-6-carboxylate[3]

A mixture of diethyl ethoxymethylenemalonate (5.25g, 24mM) and 3-aminopyrazole (2.0g, 24mM) in glacial acetic acid (20ml) was heated under reflux for two hours the resulting precipitated product was filtered and dried in vacuo. Yield 2.70g (54.0%). m.p. 292°-4° C (decomposition). ν max (nujol) 1718 (ester C=O) and 1665 (lactam C=O)cm$^{-1}$.

(b) Ethyl 4,7-dihydro-4-ethyl-7-oxo-pyrazolo[1,5-a]pyrimidine-6-carboxylate[4]

A mixture of ethyl 7-hydroxypyrazolo[1,5-a]pyrimidine-6-carboxylate (2.07g, 10mM), anhydrous potassium carbonate (1.38g, 10mM) and ethyl iodide (2.34g, 15mM) in dry N,N-dimethylformamide (50ml) was heated under reflux for 5 hours. The reaction mixture was evaporated in vacuo to given an oil, which was dissolved in water (50ml) and the pH adjusted to 1.0 with 5N hydrochloric acid. The solution was extracted with chloroform and dried over anhydrous magnesium sulphate. The chloroform extract was evaporated in vacuo and the residue was recrystallised from acetone. Yield 980 mg (41.7%). m.p. 164°-5° C. δ (DMSO-d$^6$), 8.89 (1H, s, O ), 8.13 (1H, d, N———N, J= 2.5 Hz), 6.72 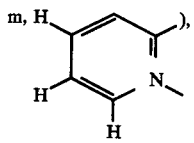

(1H d, N———N, J= 2.5 Hz), 4.36 (4H, q, —CH$_2$CH$_3$), 1.45 (3H, t, —CH$_2$CH$_3$), 1.33 (3H, t, —CH$_2$CH$_3$); νmax (nujol) 17.12 (ester C=O), 1680 (lactam C=O)cm$^{-1}$ (Found: C, 56.21; H, 5.67; N, 18.13%. C$_{11}$H$_{13}$N$_3$O$_3$ requires C, 56.12; H, 5.57; N, 17.80%).

(c) 4,7-Dihydro-4-ethyl-7-oxo-pyrazolo[1,5-a]pyrimidine-6-carboxylic acid[4]

Ethyl 4,7-dihydro-4-ethyl-7-oxo-pyrazolo[1,5-a]pyrimidine-6-carboxylate (7.42g, 31.5mM) was hydrolysed by stirring with 5% sodium hydroxide solution (50ml) at room temperature for sixteen hours. The solution was acidified with 1N hydrochloric acid and evaporated to dryness. The residue was extracted with boiling acetone, then recrystallised from ethanol, Yield 2.19g; (33.5%). m.p. 188°-9° C. δ (DMSO-d$^6$), 12.70 (1H, broad s, —COOH, exchanges with D$_2$O), 9.00 (1H, s, O ), 8.23 (1H, d, J=2.5Hz), 6.83 (1H, d, N———N), (J=2.5Hz), 4.40 (2H, q, —NCH$_2$CH$_3$), 1.46 (3H, t, —CH$_2$CH$_3$); νmax (nujol) 1740 (acid C=O) 1643 (lactam C=O)cm$^{-1}$ (Found: C, 52.09; H, 4.59; N, 20.22% C$_9$H$_9$N$_3$O$_3$ requires C, 52.17; H, 4.38; N, 20.28%).

(d) 4,7-Dihydro-4-ethyl-7-oxo-pyrazolo[1,5-a]pyrimidine-6-carboxylic acid N-hydroxysuccinimide ester A solution of 4,7-dihydro-4-ethyl-7-oxo-pyrazolo[1,5-a]pyrimidine 6-carboxylic acid (117mg, 0.5mM) and N-hydroxysuccinimide (58mg, 0.5mM) in dry N,N-dimethylformamide (2ml) was cooled to 5° C and treated with dicyclohexylcarbodiimide (103mg, 0.5mM) and stirred at this temperature for one hour then left in the fridge overnight. The reaction mixture was treated with a few drops of glacial acetic acid then filtered and evaporated in dryness. The gummy residue was dissolved in ethyl acetate and washed with water, sodium bicarbonate solution and brine and was then dried over anhydrous magnesium sulphate and evapoated to dryness. Yield 120mg (69.8%) m.p. 216°-8° C; νmax (nujol) 3330 (NH str.) 1810, 1780, 1730 (ester C=O), 1695 (urethane C=O)cm$^{-1}$. (e) 6-D-[2-(4,7-dihydro-4-ethyl-7-oxo-pyrazolo[1,5-a]pyrimidine-6-carboxamido)-2-phenylacetamido]penicillanic acid A solution of anhydrous ampicillin (175mg., 0.5mM) in dry methylene chloride (5ml) with triethylamine (0.16ml., 1.2mM) was treated with a solution of 4,7-dihydro-4-ethyl-7-oxo-pyrazolo-[1,5-a]pyrimidine-6-carboxylic acid N-hydroxysuccinimide ester (150mg., 0.5mM) in dry N,N-dimethylformamide (1ml) and stirred at room temperature for 3½ hours. The reaction mixture was evaporated to dryness and the residue dissolved in ethyl acetate (25ml). This solution was covered with water (20ml) and the pH adjusted to 2.0 with 1N hydrochloric acid. The organic layer was washed with water and then extracted with 0.1N sodium bicarbonate solution. This extract was covered with ethyl acetate and readjusted to pH 2.0 with 1N hydrochloric acid. The ethyl acetate layer was washed with brine, dried ovr magnesium sulphate, filtered, and evaporated to dryness. Yield 110mg., (35.3%). Thin layer chromatography (chloroform/acetone/acetic acid; 50:50:7 and butanol/acetic acid/water 12:3:5) revealed one component and a single zone of inhibition against *Bacillus subtilis* in butanol/ethanol/water (4:1:5 top phase) at R$_f$ = 0.44. δ (DMSO-d$^6$) 10.12 (1H, d, NH), 9.53 (1H, d, NH), 8.95 (1H, s, O ), 8.27 (1H, d, N——N

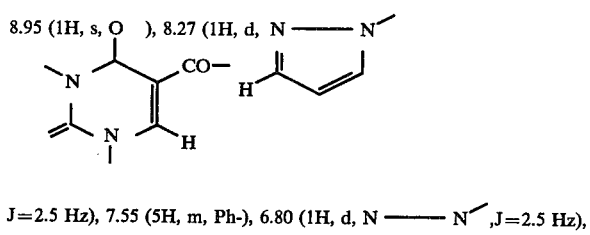

J=2.5 Hz), 7.55 (5H, m, Ph-), 6.80 (1H, d, N——N, J=2.5 Hz), 6.10 (1H,d, α-CH), 5.60 (2H,m, β-lactam), 4.35 (3H,m, H$_3$ and NCH$_2$CH$_3$), 1.55 (9H,m, gem dimethyls and —CH$_2$CH$_3$); νmax (nujol) 1780 (β-lactam C=O)cm$^{-1}$; λmax (NaHCO$_3$ solution) 280nm (ϵm 10,613) and 313nm (ϵm 8,349).

EXAMPLE 3

6-D-[2-(7-Hydroxypyrazolo[1,5-a]pyrimidine-6-carboxamido)-2-phenylacetamido]penicillanic acid (a) 7-Hydroxypyrazolo[1,5-a]pyrimidine-6-carboxylic acid A mixture of ethyl 7-hydroxypyrazolo[1,5-a]pyrimidine-6-carboxylate (0.50g., 2.4mM) and 10% sodium hydroxide solution (5ml) was heated on a steam bath for 3 hours. The reaction mixture was cooled and acidified with acetic acid to give the required product as white crystals in 76.3% weight yield (0.33%), m.p. 319°-320° C (decomposition), νmax (nujol) 1740 (acid C=O) and 1675 (lactam C=O)cm$^{-1}$.

6-D-[2-(7-Hydroxypyrazolo[1,5-a]pyrimidine-6-carboxamido)-2-phenylacetamido]penicillanic acid A suspension of 7-hydroxypyrazolo[1,5-a]pyrimidine-6-carboxylic acid (1.80g., 10mM), in dry distilled methylene chloride (60ml) with triethylamine (3.0ml., 20mM) was cooled to −30° C and treated, dropwise, with a 12.5% solution of phosgene in toluene (8.8ml., 10mM). The reaction mixture was stirred at this temperature for 10 minutes and was then treated, all at once, with a solution of anhydrous ampicillin (3.50g., 10mM) in dry distilled methylene chloride (40ml) with triethylamine (4.4ml., 30mM). The reaction mixture was allowed to reach 0° C and was then stirred at this temperature for 3 hours. The reaction mixture was filtered and the clear filtrate was evaporated to dryness then dissolved in 0.1N potassium carbonate colution (200ml). This solution was washed with ethyl acetate (3 × 200ml), filtered through Celite and was adjusted to pH 1.8 with 1N hydrochloric acid. The precipitate was filtered off and was thoroughly washed with cold water and dried in vacuo to give the required product in 36.8% weight yield (1.85g). Thin layer chromatography (chloroform/acetic acid/water; 50:50:7 and butanol/acetic acid/water; 12:3:5) revealed on component, and a single zone of inhibition against *Bacillus subtilis* in butanol/ethanol/water (4:1:5 top phase) at Rf = 0.29 δ (DMSO-d$^6$), 10.17 (1H, d, NH), 9.53 (1H, d, NH), 8.89 (1H,s, OH ), 8.25 (1H, d, N——N—,J=2.5Hz), 7.60

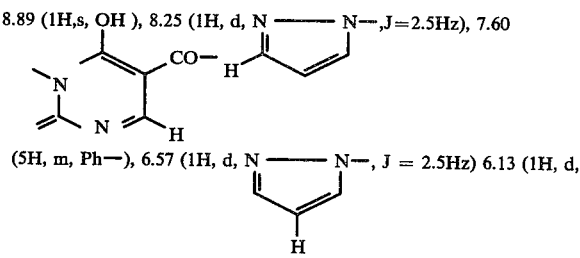

(5H, m, Ph—), 6.57 (1H, d, N——N—, J = 2.5Hz) 6.13 (1H, d,

α-CH), 5.70 (2H,m, β-lactam), 4.35 (1H, s, H$_3$) 1.63 (3H,s, —CH$_3$), 1.50 (3H,s, —CH$_3$); νmax (KBr disc) 1775 (β-lactam)cm$^{-1}$; λmax (NaHCO$_3$ solution) 310nm (ϵm 15,760).

EXAMPLE 4

6-D-[2-(5 Oxo-5H-thiazolo[3,2-a]pyrimidine-6-carboxamido)-2-phenylacetamido]penicillanic acid (a) Ethyl 5-oxo-5H-thiazolo[3,2-a]pyrimidine-6-carboxylate A solution of 2-aminothiazole (10g., 100mM) and diethyl ethoxymethylenemalonate (21.6g., 100mM) in 1,2,4-trichlorobenzene (100ml) was heated at 150° C for 4 hours with collection of evolved ethanol. The reaction mixture was cooled and the required product filtered off and recrystallised from ethanol in 75.9% weight yield (17.0g). δ (CDCl$_3$), 8.98 (1H,s, H$_5$), 8.33 (1H,d, H$_1$, J = 5.0Hz), 7.40 (1H,d, H$_2$, J = 5.0Hz), 4.47 (2H,q, —C$\underline{H}_2$CH$_3$), 1.41 (3H,t, —CH$_2$C$\underline{H}_3$); λmax (MeOH) 235nm (εm 5000), 258nm (εm 4,550) and 346nm (εm 13,500); (Found: C, 47.84; H, 3,42; N, 12.19; S, 14.54%. C$_9$H$_8$N$_2$O$_3$S requires C, 48.22; H, 3.60; N, 12.50; S, 14.28%).

(b) 5-oxo-5H-thiazolo[3,2-a]pyrimidine-6-carboxylic acid

A mixture of ethyl 5-oxo-5H-thiazolo[3,2-a]pyrimidine-6-carboxylate (11.2g., 50mM) and 2N hydrochloric acid (75ml) was heated under reflux for 5 hours. The reaction mixture was cooled and filtered to give the required product in 79.7% weight yield (7.81g). νmax (KBr disc) 1720 (acid C=O)cm$^{-1}$; λmax (NaHCO$_3$ solution) 232nm (εm 2650), 263nm (εm 2030), 328nm (εm 6000) and 339nm (εm 5400); (Found: C, 43,65; H, 2.26; N, 14.16; S, 16.62%. C$_7$H$_4$N$_2$O$_3$S requires C, 43.87; H, 2.06; N, 14.28; S, 16.32%.

(c) 6-D-[2-5-Oxo-5H-thiazolo[3,2-a]pyrimidine-6-carboxamido]-2-phenylacetamido]penicillanic acid A solution of 5-Oxo-5H-thiazolo[3,2-a]pyrimidine-6-carboxylic acid (0.49g., 2.5mM) in dry distilled methylene chloride (25ml) with triethylamine (1.42ml, 10mM) was cooled to −10° C and treated with isobutyl chloroformate (0.32ml, 2.5mM). The reaction mixture was stirred at this temperature for a further 5 minutes, then treated with a chilled solution of anhydrous ampicillin (0.87g, 2.5mM) in methylene chloride (20ml) with triethylamine (0.70ml, 5mM). The stirred solution was allowed to reach room temperature (ca 1 hour) and was then evaporated to dryness and the residue dissolved in water (100ml). This aqueous solution was washed with ethyl acetate (2 × 100ml) then covered with ethyl acetate (100ml) and acidified with 1N hydrochloric acid to pH 2.0. This organic extract was washed with water, brine, dried over anhydrous magnesium sulphate, filtered and evaporated to dryness. The required product was obtained in 34.2% weight yield (450mg). Thin layer chromatography (chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf 0.31. δ (DMSO-d$^6$), 10.03 (1H,d, NH), 9.50 (1H,d, NH), 8.93 (1H,s, O), 8.42 (1H,d, 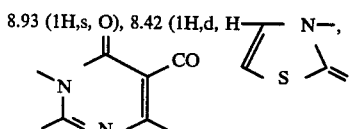

J = 5.0Hz), 7.89 (1H,d, 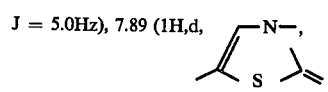

J = 5.0Hz), 7.53 (5H,m, Ph), 6.10 (1H,d, α-CH), 5.54 (2H,m, β-lactam), 4.31 (1H,s, H$_3$), 1.57 (3H,s, CH$_3$), 1.42 (3H,s, CH$_3$); νmax (KBr disc) 1775 (β-lactam C=O)cm$^{-1}$.

EXAMPLE 5

6-D-[2-(7-Hydroxy-1,2,4-triazolo[1,5-a]pyrimidine-6-carboxamido)-2-phenylacetamido]penicillanic acid (a) Ethyl 7-hydroxy-1,2,4-triazolo[1,5-a]pyrimidine-6-carboxylate A mixture of 3-amino-1,2,4-triazole (8.4g, 100mM) and diethyl ethoxymethylenemalonate (24.0g, 110mM) in glacial acetic acid (150ml) was heated under reflux for six hours. The resulting precipitated product was filtered and dried in vacuo. Yield 8.20g (36.6%). δ (DMSO-d$^6$), 12.85 (1H,s, —OH), 8.87 (1H,s, H$_2$), 8.56 (1H,s, H$_5$), 4.38 (2H,q,—C$\underline{H}_2$CH$_3$), 1.34 (3H,t, —CH$_2$C$\underline{H}_3$); νmax (KBr disc) 1730 (ester C=O)cm$^{-1}$; (Found: C, 45.99; H, 3.94; N, 27.29%. C$_8$H$_8$N$_4$O$_3$ requires C, 46.16; H, 3.87; N, 26.91%).

(b) 7-Hydroxy-1,2,4-triazolo[1,5-a]pyrimidine-6-carboxylic acid

A mixture of ethyl 7-hydroxy-1,2,4-triazolo[1,5-a]pyrimidine-6-carboxylate (5.6g. 25mM) and 2N hydrochloric acid (40ml) was heated under reflux for 5 hours. The reaction mixture was cooled and filtered to give the required product in 67.3% weight yield (3.30g). m.p. 296° C (decomposition). νmax (KBr disc) 1725 (acid C=O)cm$^{-1}$; λmax (NaHCO$_3$ solution) 293nm (εm 14,900); (Found: C, 40.27; H, 2.35; N, 30.49%. C$_6$H$_4$N$_4$O$_3$ requires C, 40.01; H, 2.24; N, 31.10%).

(c) 6-D-[2-(7-Hydroxy-1,2,4-triazolo[1,5-a]pyrimidine-6-carboxamido)-2-phenylacetamido]penicillanic acid A solution of 7-hydroxy-1,2,4-triazolo[1,5-a]pyrimidine-6-carboxylic acid (0.90g, 5mM) in dry distilled methylene chloride (30ml) with triethylamine (1.5ml., 10mM) was cooled to −30° C and treated, dropwise, with a 12.5% solution of phosgene in toluene (4.4ml., 5mM). The reaction mixture was stirred at this temperature for 10 minutes and was then treated, all at once, with a solution of anhydrous ampicillin (1.75g, 5mM) in methylene chloride (20ml) with triethylamine (2.2ml, 15mM). The reaction mixture was allowed to reach 0° C and was then stirred at this temperature for 3 hours. The reaction mixture was filtered and the clear filtrate was evaporated to dryness then dissolved in 0.1N potassium carbonate solution (100ml). The solution was washed with ethyl acetate (3 × 100ml), filtered through Celite and was adjusted to pH 2.0 with 1N hydrochloric acid in the presence of ethyl acetate (100ml). The organic extract was washed with water, brine, dried over anhydrous magnesium sulphate, filtered and evaporated to dryness. The required product was obtained in 52.6% weight yield (1.35g). Thin layer chromatography (chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf = 0.23. δ (DMSO-d$^6$), 10.06 (1Hd, NH), 9.60 (1H,d, NH),

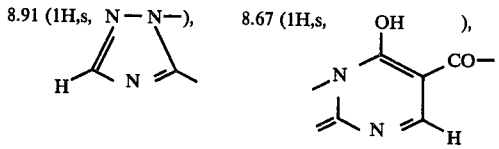

7.58 (5H,m, Ph—), 6.13 (1H,d, α-CH), 5.67 (2H,m, β-lactam), 4.35 (1H,s, H$_3$) 1.63 (3H,s, CH$_3$), 1.50 (3H,s, CH$_3$); νmax (KBr disc), 1770 (β-lactam C=O)cm$^{-1}$; λmax (NaHCO$_3$ solution), 297nm (εm 17,170).

EXAMPLE 6

6-D-[2-(4,7-Dihydro-4-ethyl-7-oxo-pyrazolo[1,5-a]pyrimidine-6-carboxamido)-2-p-hydroxyphenylacetamido]penicillanic acid A solution of 4,7-dihydro-4-ethyl-7-oxo-pyrazolo[1,5-a]pyridimine-6-carboxylic acid (520mg, 2.5mM) in dry N,N-dimethylacetamide (10ml) with triethylamine (0.35ml, 2.5mM) was cooled to −10° C and treated with isobutyl chloroformate (0.32ml, 2.5mM). The reaction mixture was stirred at this temperature for 10 minutes, then treated with a chilled solution of D-α-amino-p-hydroxybenzylpenicillin trihydrate (1.05g, 2.5mM) in 0.5 N sodium hydroxide solution (5ml). The stirred solution was allowed to reach room temperature (ca 1 hour) and was then evaporated at reduced pressure. The resulting residue was dissolved in 0.1 N sodium bicarbonate solution (50ml) and was washed with ethyl acetate (2 × 150ml) then covered with ethyl acetate (200ml) and acidified with 1N hydrochloric acid to pH 2.0. This organic extract was washed with 0.1N hydrochloric acid, water, brine, dried over anhydrous magnesium sulphate, filtered and evaporated to dryness. The required product was obtained in 36.1% weight yield (500mg). Thin layer chromatography (chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf 0.28. δ (DMSO-d$^6$) 9.89 (1H,d, NH), 9.20 (1H, d, NH), 8,80 (1H,s, CO), 8.11 (1H,d,

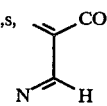N—, J 2.5 Hz), 7.33 and 6.79 (4H, AA', BB', 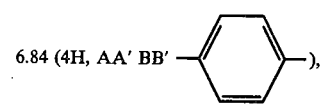), 6.71

(1H,d, N—, J 2.5 Hz), 5.88 (1H,d, α-CH), 5.55 (2H,m, β-lactam), 4.20 (3H, m, H$_3$ and —NCH$_2$CH$_3$), 1.50 (9H,m, gem dimethyls and —CH$_2$CH$_3$): νmax 1770 (β-lactam C=O)cm$^{-1}$; λmax. (NaHCO$_3$ solution) 279nm (εm 14,900) and 311nm (εm 10,750).

EXAMPLE 7

6-D-[2-(7-Hydroxy-1,2,4-triazolo[1,5-a]pyrimidine-6-carboxamido)-2-p-hydroxyphenylacetamido]penicillanic acid A solution of 7-hydroxy-1,2,4-triazolo[1,5-a]pyrimidine-6-carboxylic acid (450mg, 2.5mM) in dry distilled methylene chloride (25ml) with triethylamine (0.75ml, 5mM) was cooled to −30° C and treated, dropwise with a 12.5% solution of phosgene in toluene (2.2ml, 2.5mM). The reaction mixture was stirred at this temperature for 10 minutes and was then treated, all at once, with a solution of D-α-amino-p-hydroxybenzyl penicillin triethylamine salt (1.165g, 2.5mM) in dry distilled methylene chloride (25ml). (The addition of a few drops of triethylamine was necessary to give complete solution of the triethylamine salt). The reaction mixture was allowed to reach 0° C and was then stirred at this temperature for 3 hours. The reaction mixture evaporated at reduced pressure and the resulting residue dissolved in 0.1 N sodium bicarbonate solution (50ml). This aqueous solution was washed with ethyl acetate (50ml) then acidified with 1N hydrochloric acid to pH 2.5. The resulting precipitate was removed by filtration, washed with water and dried in vacuo. The required product was obtained in 25.8% weight yield (340mg). Thin layer chromatography (chloroform/acetic acid/water; 50:50:7 and butanol/acetic acid/water; 12:3:5) revealed one component, and a single zone of inhibition against *Bacillus subtilis* in butanol/acetic acid/water (12:3:5) at Rf 0.72. δ (DMSO-d$^6$), 9.76 (1Hd, NH). 9.32 (1H d, NH), 8.74

(1H,s, N—), 8.38 (1H,s, CO), 7.39 and 6.84 (4H, AA' BB'), 5.80 (1H, d, α-CH), 5.55 (2H, m, β-lactam), 4.27 (1H, s, H$_3$), 1.53 (3H, s, CH$_3$), 1.44 (3H, s, CH$_3$); νmax (KBr disc) 1770 (β-lctam C=O)cm$^{-1}$; λmax (NaHCO$_3$ solution) 268nm (εm 7,130) and 296nm (εm 14,150).

EXAMPLE 8

6-D-[2-(5-Oxo-5H-thiazolo[3,2-a]pyrimidine-6-carboxamido)-2-p-hydroxyphenylacetamido]penicillanic acid A solution of 5-oxo-5H-thiazolo[3,2-a]pyrimidine-6-carboxylic acid (490mg, 2.5mM) in dry distilled methylene chloride (25ml) with triethylamine (1.42ml, 10mM) was cooled to −10° C and treated with isobutyl chloroformate (0.32ml, 2.5mM). The reaction mixture was stirred at this temperature for 10 minutes, then treated with a chilled solution of D-α-amino-p-hydroxybenzylpenicillin triethylamine salt (1.165g, 2.5mM) in dry distilled methylene chloride (20ml) (The addition of a few drops of triethylamine was necessary to give complete solution of the triethylamine salt.) The stirred solution was allowed to reach room temperature (ca 1 hour) and was then evaporated to dryness and the residue dissolved in 0.1 N sodium bicarbonate solution (50 ml). The aqueous solution was washed with ethyl acetate (50ml) then covered with ethyl acetate (100ml) and acidified with 1 N hydrochloric acid to pH 2.5. This organic extract was washed with water, brine, dried over anhydrous magnesium sulphate, filtered and evaporated to dryness. The required product was obtained in 50.1% weight yield (680mg). Thin layer chromatography (chloroform/acetic acid/water; 50:50:7 and butanol/acetic acid/water; 12:3:5) revealed one component, and a single zone of inhibition against *Bacillus subtilis* in butanol/ethanol/water (4:1:5 top phase) at Rf 0.18. δ (DMSO-d$^6$), 9.24 (1H, d, NH), 8.77 (1H,s, CO), 8.30 (1H,d, H , J=5Hz), 7.74

(1H,d, 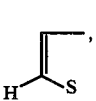 , J=5Hz), 7.33 and 6.79

(4H, AA' BB', 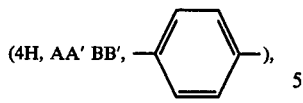), 5.83 (1H, d, α-CH), 5.60 (2H, m, β-lactam), 4.21 (1H, s, 3-H), 1.57 (3H, s, CH₃), 1.44 (3H, s, CH₃); νmax (KBr disc) 1775 (β-lactam C=O)cm⁻¹; λmax (NaHCO₃ solution) 231nm (εm 17,040), 262nm (εm 5,850), 331nm (εm 18,600) and 342nm (εm 19,300).

EXAMPLE 9

6-D-[2-(7-Hydroxypyrazolo[1,5-a]pyrimidine-6-carboxamido)2-p-hydroxyphenylacetamido]penicillanic acid

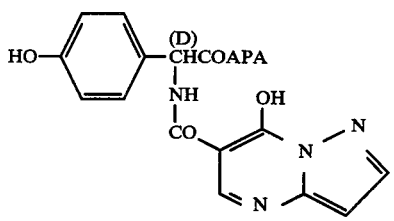

To a suspension of 7-hydroxy-pyrazolo-[1,5-a]pyrimidine-6-carboxylic acid (0.9g, 0.005 M) in dry methylene chloride (50 ml) and triethylamine (3.0ml, 0.02 M) at −30° C was added 12.5% phosgene in toluene (4.4m., 0.005 M). After stirring at −30° C for 20 minutes it was treated with a solution of triethylammonium salt of amoxycillin (.233g, 0.005 M) in methylene chloride (25ml), triethylamine (1.5ml, 0.0 M) and chlorotrimethylsilane (2.4ml, 0.019 M) which had been refluxed under nitrogen for 30 minutes. The reaction mixture was stirred under nitrogen at 0° C for 3 hours and then filtered. After evaporation of filtrate and dissolving the residue in water at pH 8, the crude product (0.85g) was obtained by adjusting pH to 1.5 and filtering off the solid. The product was contaminated with triethylammonium chloride and was purified by dissolving the crude product (0.5g) in sodium bicarbonate solution (pH 8.5) and reprecipitating the product (0.15g, 10%). νmax (KBr) 3300 (br), 1770, 1728, 1664, 1620, 1582, 1508 and 787cm⁻¹; δ [(CD₃)₂SO] 1.42 (s) and 1.57 (s) (gem dimethyls), 4.20 (s) (C₃ proton), 5.30–5.65 (m) (β-lactams), 5.80 (d), (α-CH, J=8 Hz), 6.35 (d) (N—N—, J=2 Hz), 6.71 (d) and 7.25

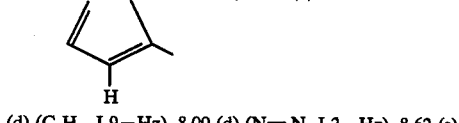

(d) (C₆H₄, J 9=Hz), 8.00 (d) (N—N, J 2=Hz), 8.62 (s)

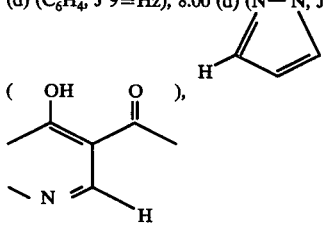

9.15 (d) and 9.75 (d) (2 × CONH); λmax, (NaHCO₃) 222 (ε 2100) and 310nm (13,600), biochromatogram (B/E/W) single zone Rf 0.26, hydroxylamine assay (penicillin G) 78%.

EXAMPLE 10

D-α-(8-Methoxy-4-oxo-4H-pyrimido[2,1-b]benzothiazol-3-carbonylamino)benzyl penicillin 8-Methoxy-4H-pyrimido[2,1-b]benzothiazol-4-one-3-carboxylic acid (1.32g, 0.005 M) in methylene chloride (25ml) and triethylamine (0.7ml), cooled to −10° C was heated with ethyl chloroformate (0.48ml) and stirred at −10° C for 30 minutes. A solution of anhydrous ampicillin (1.75g, 0.005M) in methylene chloride (25ml) and triethylamine (1.4ml) was added all at once and the mixture stirred at room temperature for 1 hour. Solvent was evaporated and the residue mixed with water (30ml) and ethyl acetate (30ml). The pH was adjusted to 1.5 with N hydrochloric acid. The insoluble solid produced, was filtered, washed with water and ethyl acetate and dried to give the penicillin free acid 2.6g (85.7%) as a colourless non-crystalline solid. δ [CD₃)₂SO] 1.52 (6H, d, gem dimethyls), 3.86 (3H, s, —OCH₃), 4.27 (1H, s, C₃-proton), 5.52 (2H, m, β-lactam protons), 6.01 (1H, d, α-proton), 7.40 (7H, m, aromatic protons), 8.71 (1H, s, pyrimidine proton), 8.87 (1H, d, aromatic proton), 9.35 (1H, d, CONH), 9.94 (1H, d, CONH).

EXAMPLE 11

D,α-(5-Oxo-5H-thiazolidino[3,2-a]pyrimidin-6-carbonylamino)benzyl penicillin

5-Oxo-thiazolidino[3,2-a]pyrimidine-6-carboxylic acid 1g (0.005 M) in methylene chloride (25ml) and triethylamine (0.9ml) cooled to −10° C was treated with ethyl chloroformate (0.48ml) and stirred at −10° C for 30 minutes. A solution of anhydrous ampicillin in methylene chloride (25ml) and triethylamine (1.4ml) was added all at once and stirred at room temperature for 1 hour. The solution was evaporated and the residue dissolved in water (25ml) and washed with ethyl acetate (25ml). The aqueous layer was covered with fresh ethyl acetate and adjusted to pH 1.5 with 5N HCl. The organic layer was separated and the aqueous layer re-extracted with ethylacetate. The combined organic extracts were dried and treated with 2H sodium 2-ethylhexoate in methylisobutylketone (2ml). The separated solid was filtered, washed with ethyl and dried to give the penicillin sodium salt 1.76g (63.9%). δ [(CD₃)₂SO] 1.50 (6H, d, gem dimethyls), 3.60 2H, t, (thiazoline methylene), 3.94 (1H, s, C3-proton), 4.56 (2H, t, thiazoline methylene), 5.44 (2H, m, β-lactam protons), 5.98 (1H, d, α-proton), 7.44 (5H, s, aromatic protons), 8.53 (1H, s, pyrimidine proton), 9.20 (1H, d, CONH), 9.90 (1H, d, CONH).

EXAMPLE 12

D,α-(5-Oxo-5H,thiazolidino[3,2-a]pyrimidin-6-carbonylamino)-p-hydroxybenzyl penicillin 5-Oxothiazolidino[3,2-a]pyrimidin-6-carboxylic acid (1g, 0.005 M) in methylene chloride (25ml) and triethylamine (0.9ml) cooled to −10° C was treated with ethyl chloroformate (0.48ml) and stirred at −10° C for 30 minutes. A solution of triethylammonium D,α-amino-p-hydroxybenzylpenicillanate (2.3g, 0.005 M) in methylene chloride (25ml) and triethylamine (0.7ml) was added all at once and the solution stirred at room temperature for 1 hour. The product was worked up as described in the previous example to give the penicillin sodium salt 2.18g (77%) was a colourless non-crystalline solid. δ[CD₃)₂SO]0 1.50 (6H, d, gem dimethyls), 3.61 (2H, t, thiazoline methylene), 4.04 (1H, s, C3-proton), 4.52 (2H, t, thiazoline methylene), 5.37 (2H, m, β-lactam protons), 5.79 (1H, d, α-proton), 7.00 (4H, q, p-substituted aromatics), 8.50 (1H, s, pyrimidine proton) 9.04 (1H, d, CONH), 9.74 (1H, d, CONH).

EXAMPLE 13

D,α-(8-Methoxy-4-oxo-4H-pyrimido[2,1-b]benzothiazol-3-carbonylamino)-p-hydroxybenzyl penicillin 8-Methoxy-4H-pyrimido[2,1-b]benzothiazol-4-one-3-carboxylic acid 1.3g (0.005M) in methylene chloride (25ml) and triethylamine (0.7ml) cooled to −10° C was treated with ethyl chloroformate (0.49ml) and stirred at −10° C for 30 minutes. A solution of triethyl ammonium D,α-amino-p-hydroxy benzyl penicillanate (2.3g, 0.005 M) in methylene chloride (25ml) and triethylamine (0.7ml) was added all at once and the solution stirred at room temperature for 1 hour. The solution was evaporated, the residue dissolved in water (30ml) washed twice with ether (30ml) and covered with ethyl acetate (30ml). The pH was adjusted to 1.5 with N.NCl and a gummy solid separated. Supernatant liquid was decanted and the gum dissolved in acetone and allowed to crystallise. Solid product was filtered, washed with acetone and dried to give the penicillin free acid, 1.24g (39.8%) as a colourless crystalline solid. δ[(CD₃)₂SO] 1.56 (6H, d, gem dimethyls), 3.88 (3H, s, OCH₃), 4.27 (1H, s, C3-proton), 5.56 (2H, m, δ-lactam protons), 5.90 (1H, d, α-proton), 7.08 (4H, q, p-substituted aromatics), 7.20 (1H, m, aromatic proton), 7.73 (1H, d, aromatic proton), 8.73 (1H, s, pyrimidine proton), 8.87 (1H, d, aromatic proton), 9.25 (1H, d, CONH), 9.83 (1H, d, CONH).

EXAMPLE 14

6-(R-2-(6,7,8,9-Tetrahydro-4oxo-4H-pyrido[1,2-a]pyrimidine-3-carboxamido)-2-phenylacetamido) penicillanic acid Sodium 6,7,8,9-tetrahydro-4-oxo-4H-pyrido-[1,2-a]pyrimidine-3-carboxylate (2mM, 0.432g.) was suspended in a mixture of dry acetone (25ml) and dry dimethylacetamide (2ml) and chilled to −10° C with stirring. Ethyl chloroformate (2mM, 0.2ml) and one drop of N-methyl morpholine were added and the reaction mixture stirred 20 minutes at −10° C. A solution of ampicillin trihydrate (2mM, 0.726g) in aqueous sodium hydroxide (0.489N, 3.64ml) was chilled and added to the mixed anhydride at −10° C. The reaction was stirred 1.75 hours to ambient temperature, the acetone evaporated, and the resulting solution diluted to 100ml with water, covered with ethyl acetate (50ml) and adjusted to pH 2.0 with 5N HCl. The organic layer was separated, the aqueous phase extracted with ethyl acetate (1 × 50ml), the organic extracts combined, washed with water (3 × 30ml), dried over magnesium sulphate to give the penicillanic acid as a white solid 0.85g. (85%), showing a single component on t.l.c., Rf 0.51 (chloroform/acetone/acetic acid; 7:7:1) δ [(CD₃)₂SO] 1.4, 1.55 (6H, 2 × s, gem dimethyls), 1.7

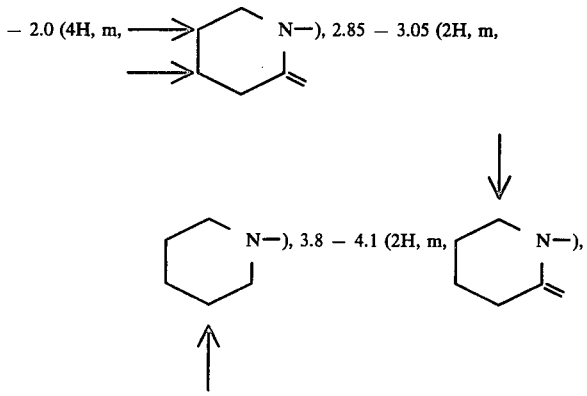

4.17 (1H, s, C₃ proton), 5.3 − 5.6 (2H, m, β-lactam protons), 5.87 (1H, d, α-proton), 7.1 − 7.5 (5H, m, aromatics), 8.5 (1H, s, pyrimidine proton), 9.2 − 10.0 (2H, 2 × d, 2 × NH); λmax (0.3% NaHCO₃ solution) 206 (ε = 25,800), 230 (ε = 12,140) and 300 n.m. (ε = 11,000).

EXAMPLE 15

D-α-(7-Oxo-7H-1,2,4-triazolo[5,1-b][1,3]thiazine-6-carbonylamino)benzylpenicillin 7-Oxo-7H-1,2,4-triazolo[5,1-b][1,3]thiazine-6-carboxylic acid hydrate (224mgs, 1.0 eq) was dissolved in dimethylformamide (3ml) and acetone (1ml) and stirred with magnesium sulphate (1.0g) for 1 hour at room temperature. After cooling to ca 5° C N-hydroxysuccinimide (125mg, 1.1eq) and dicyclohexylcarbodiimide (227mg, 1.1eq) were added and stirred at 0° to 5° C for 3 hours. The reaction mixture was stored overnight in a refrigerator and then filtered into a solution of ampicillin (314mgs, 0.9eq) in acetone (10ml) with triethylamine at 0° C. Stirring was continued at 0° to 5° C for 1½ hours and then at room temperature for 1 hour. The reaction mixture was evaporated to an oil, washed with ether then triturated with actone. After filtering off the triethylammonium salt of the required penicillin (200mgs, 35%) the free acid was obtained by dissolving a portion (130mgs) in water (15ml) and adjusting pH to 2 at 0° C and filtering off the product (50mgs, 15%), νmax (KBr) 3300(br), 1766, 1720, 1683, 1630, 1525 and 1216cm⁻¹, δ [(CD₃)₂SO] 1.38(s) and 1.52(s) (gem dimethyls), 4.17(s) (C3 proton), 5.25 − 5.60(m) (β-lactams), 5.74 (d) (PhCH), 7.1 − 7.6(m) (C₆H₅), 8.60(s) (NCHN), 9.16(s), (SCH), 9.33(d) (CONH), biochromatogram (B/E/W) Rf 0.11.

EXAMPLE 16

D,α-(3,7-Dihydro-3-amino-2-methyl-7-oxo-s-triazolo[1,5-a]pyridimine-6-carbonylamino)benzylpenicillin 3,7-Dihydro-3-amino-2-methyl-7-oxo-s-triazolo[1,5-a]pyridimine-6-carboxylic acid (1.22g, 0.005mol) in methylene chloride (25ml) and triethylamine (1.4ml) was stirred 15 minutes, cooled to −10° C and treated with ethyl chloroformate (0.48 ml). The mixture was stirred at −10° C for 30 minutes and a solution of anhydrous ampicillin (1.75g, 0.005mol) in methylene chloride (25ml) and triethylamine (1.4ml) was added all at once. The reaction mixture was stirred at room temperature for 1 hour and worked up as described in Example 10 to give the penicillin free acid. This, dissolved in ethyl acetate, was treated with sodium 2-ethylhexoate to precipitate the sodium salt 1.4g. (50%) as a colourless non-crystalline solid. δ [(CD$_3$)$_2$SO] 1.50 (6H, d, gem dimethyls), 2.55 (3H, s, triazolemethyl), 3.93 (1H,s, C$_3$ proton), 5.39 (2H,m, β-lactam protons), 6.00 (1H,d, α-proton), 6.30 (2H,m, —NH$_2$ exchanges with D$_2$O), 7.42 (5H,m, phenyl protons), 8.83 (1H,s, pyrimidine proton), 9.18 (1H,d, —CONH— exchanges with D$_2$O), 9.88 (1H, d, —CONH— exchanges with D$_2$O).

EXAMPLE 17

D-α-(4,7-Dihydro-4-ethyl-7-oxo-1,2,4-triazolo[1,5-a]pyrimidine-6-carbonylamino) p-hydroxybenzyl penicillin (a) Ethyl 4,7-dihydro-4-ethyl-7-oxo-1,2,4-triazolo[1,5-a]-pyrimidine-6-carboxylate Ethyl 7-hydroxy-1,2,4-triazolo [1,5-a]pyrimidine-6-carboxylate (10.4g, 50mM), potassium carbonate (7.0g, 50mM), ethyl iodide (8.0ml, 15mM), dry dimethylformamide (80ml) and hexamethylphosphorotriamide (80ml) was heated at 80° C for 4 hours. The resulting mixture was evaporated in vacuo and water added (100ml). The solution was washed with ether (5 × 100ml) then extracted with ethyl acetate (10 × 100ml). The ethyl acetate extracts were dried over magnesium sulphate, filtered and evaporated in vacuo. The crystals were filtered off and recrystallised from ethyl acetate. 37.9% yield (4.47g); mpt 129° – 131° C. δ (CDCl$_3$) 8.62 (1H,s) and 8.12 (1H,s),

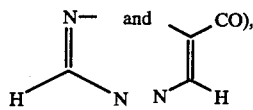

4.47 (2H,q) and 4.38 (2H,q), (OCH$_2$CH$_3$ and NCH$_2$CH$_3$), 1.62 (3H,t) and 1.50 (3H,t), (OCH$_2$CH$_3$ and NCH$_2$CH$_3$); ν max (KBr) 3400 (broad) 1715, 1690, 1610, 1570, 1480, 1370, 1325, 1210, 1175, 790cm$^{-1}$; λmax (EtOH) 209 (εm 12,400), 252 (εm 8,260) and 290 (εm 11,800)nm.

(b) 4,7-Dihydro-4-ethyl-7-oxo-1,2k,4-triazolo[1,5-a]pyrimidine-6-carboxylic acid Ethyl 4,7-dihydro-4-ethyl-7-oxo-1,2,4-triazolo[1,5-a]pyrimidine-6-carboxylate (4.7g, 20mM) in 10% sodium hydroxide solution (80ml) was stirred at room temperature for 18 hours. The solution was adjusted to pH 4.5 with 5N hydrochloric acid, and the precipitate filtered off, washed with a little cold water and dried in vacuo. 82.1% yield (3.43g) mpt 176°–180° C. δ (D$_2$O + NaOD), 7.81 (1H,s) 7.67 (Hs)

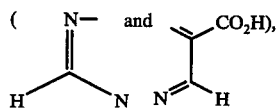

3.85 (2H,q, NCH$_2$CH$_3$) 9.18 (3H,t, NCH$_2$CH$_3$); νmax (KBr) 1750, 1570, 1625, 1608, 1560, 1480, 1240, 1185cm$^{-1}$. λmax (NaHCO$_3$ soln) 255 (εm 6,940) and 298 (εm 9220)nm. (Found: C, 41.12; H, 3,97; N, 24.32%; C$_8$H$_9$N$_4$O$_3$ requires C, 45.97; N, 4.35; N, 26.81%).

(c) D-α-(4,7-Dihydro-4-ethyl-7-oxo-7H-1,2,4-triazolo[1,5-a]pyrimidine-6-carbonylamino) p-hydroxy-benzyl penicillin 4-7-Dihydro-4-ethyl-7-oxo-1,2,4-triazolo[1,5-a]pyrimidine-6-carboxylate triethylammonium salt (0.776g, 2.5 mM) in hexamethylphosphorotriamide (25ml) and triethylamine (0.70ml, 10mM) was cooled to −10° C and treated dropwise with isobutylchloroformate (0.32ml, 2.5mM). The reaction mixture was stirred at this temperature for 10 minutes, then treated with a solution of D-α-amino-p-hydroxy-benzylpenicillin triethylammonium salt (1.16g, 1.5mM) in dry distilled methylene chloride (40Ml) (The addition of a few drops of triethylamine was necessary to give complete solution of the triethylammonium salt). The stirred solution was allowed to reach room temperature (ca 1 hour) and was evaporated at reduced pressure. Sodium bicarbonate solution (0.1N, 25ml) was added to the residue, and this aqueous solution was washed with ethyl acetate (2 × 25ml) then layered with ethyl acetate (50ml) and acidified with 5N hydrochloric acid to pH 2.5 The aqueous phase was further extracted with ethyl acetate (3 × 50ml). The ethyl acetate extracts were then extracted into sodium bicarbonate solution bicarbonate solution (3 × 60ml), the aqueous solution adjusted to pH 7.0 with 1N hydrochloric acid and continuously extracted with ether for 1 hour. The aqueous phase was then layered with ethyl acetate (200ml) and acidified to pH 2.5 with 5N hydrochloric acid. The aqueous phase was further extracted with ethyl acetate (2 × 100ml). The bulked organic extracts were washed with 0.1N hydrochloric acid, water, brine, dried over anhydrous magnesium sulphate, filtered, and evaporated to dryness. The required product acid/water; 12:3:5) revealed one component, and a single zone at inhibition against *Bacillus subtilis* in butanol/ethanol/water (4:1:5 top phase) at Rf 0.24. δ (DMSO-d$^6$) 9.50 (1H,d, NH), 9.08 (1H,d, NH), 8.83 (1H,s), and 8.34 (1H,s),

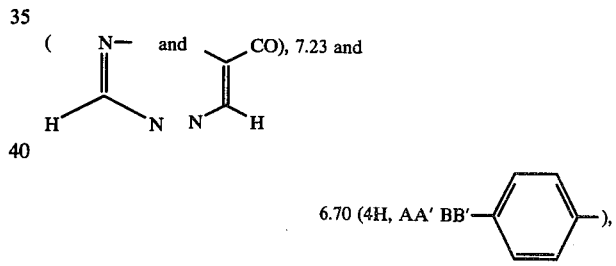

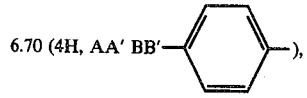

5.83 (1Hd, α-CH), 5.45 (2H,m, β-lactams), 4.08 (1H,s, 3-H), 1.52 (3H,s, C$_3$), 1.38 (3H,s, CH$_3$); νmax (KBr disc) 1775 (β-lactam C=O)cm$^{-1}$; λmax (NaHCO$_3$ solution) 205 (εm 32,200), 255 (εm 8,640) and 291 (εm 11,200)nm.

EXAMPLE 18

D-α-(7-Hydroxy-tetrazolo[1,5-a]pyrimidine-3-carbonyl-amino)-benzyl penicillin is prepared by the method as described in Example 16.

EXAMPLE 19

D,α-(4-Oxo-4H-pyrido[2,1-c]as-triazine-3-carbonylamino)benzyl penicillin (a) Pyrid-2-ylhydrazone of diethyl ketomalonate 2-Hydrazinopyridine (11g, 0.1mol) mixed with diethyl ketomalonate (24g) in ethanol (80ml) was heated at reflux for 3½ hours. The orange solution was evaporated to small volume and allowed to crystallise. The yellow crystalline solid was filtered, washed with ethanol and dried to give 17.9g (67.6%) of the product mp 65°–7°. δ [(CD$_3$)$_2$SO] 1.36 (6H, t 2 × CH$_3$CH$_2$—), 4.38 (4H,m, 2 × CH$_3$CH$_2$—), 7.0–8.5 (4H,m, pyridine protons), 12.11 (1H,s —NH— exchanges with D$_2$O).

(b) Ethyl 4-oxo-4H-pyrido[2,1-c]-as-triazine-3-carboxylate

The hydrazone from (a) above (17.9g) in 1,2,4-trichlorobenzene (75ml) was heated at 220° C for 2 hours removing ethanol as it was formed. The brown solution was cooled and diluted with an equal volume of petroleum ether 60°-80° C and allowed to crystallise. The product was filtered and recrystallised, from methanol to give 4.3g of ester m.p. 130°-132° C. δ [(CD$_3$)$_2$SO] 1.40 (3H,t, CH$_3$CH$_2$—), 4.45 (2H,q, CH$_3$CH$_2$—), 7.70 (1H,m, pyridine proton), 8.20 (2H,m, pyridine protons), 9.06 (1H,m, pyridine proton). λmax (MeOH) 211 (ε = 12,700), 276 (ε = 8,400) and 376nm (ε = 14,900). Found: C, 54.59; H, 4.13; N, 19.37. C$_{10}$H$_9$N$_3$O$_3$ required: C, 54.80; H, 4.14; N, 19.17%.

(c) 4-Oxo-4H-pyrido[2,1-c]-as-triazine-3-carboxylic acid

Ethyl ester from (b) above (0.22g, 0.001mol) in 0.5N NaOH (2ml) was heated on a steam bath for 2 hours. The brown solution was cooled and acidified with 5N HCl. The separated solid was filtered washed with water, methanol and acetone to give 0.1g (52%) of product mp. 190° (d). Found: C, 46.05; H, 3.48; N, 19.91. C$_8$H$_5$N$_3$O$_3$. H$_2$O required: C, 45.94; H, 3.37; N, 20.09%.

(d) Penicillin

4-Oxo-4H-pyrido[2,1-c]-as-triazine-3-carboxylic acid (0.48g, 0.0025ml) in thionyl chloride (5ml) was heated at 70° C for 1 hour. Excess thionyl chloride was distilled off under vacuum and the residue dissolved in methylene chloride (10ml). The solution was added all at once at 0° C to a solution of anhydrous ampicillin (0.88g, 0.0025mol) in methylene chloride (10ml) and triethylamine (0.1ml). The reaction solution was stirred for 1 hour and evaporated under reduced pressure. The residue, dissolved in water (20ml) was washed with ether, covered with ethyl acetate and acidified with stirring, to pH 1.5 with 5N hydrochloric acid. The layers were separated and the aqueous layer re-extracted with ethyl acetate. The combined organic extracts were dried over anhydrous magnesium sulphate and treated with 2N sodium 2-ethylhexoate in methylisobutylketone until precipitation ceased. The solid was filtered, washed with dry ether and dried in vacuo to give the penicillin sodium salt 0.34g (25%) as a colourless noncrystalline solid. δ [(CD$_3$)$_2$SO] 1.53 (6H,d, gem dimethyls), 3.96 (1H,s, C$_3$ proton), 5.40 (2H,m, β-lactam protons), 5.93 (1H,d, α-proton), 6.96 (1H,m, pyridine proton), 7.40 (7H,m, phenyl + pyridine protons) 8.2 (1H,m, pyridine proton), 9.13 (1H,d, —CONH— exchanges with D$_2$O), 9.7—(1H,d, —CONH— exchanges with D$_2$O).

EXAMPLE 20

D,α-(7-Chloro-4-oxo-4H-pyrimido[2,1-b]benzoxazole-3-carbonylamino)benzyl penicillin 7-Chloro-4-oxo-4H-pyrimido[2,1-b]benzoxazole-3-carboxylic acid (0.7g, 0.0025mol) was treated with thionyl chloride then coupled with anhydrous ampicillin as described in Example 19(d) to give the penicillin sodium salt in 35.6% yield; δ [(CD$_3$)$_2$SO/D$_2$O] 1.44 (6H,d, gem dimethyls), 4.00 (1H,s, C$_3$ proton), 5.37 (2H,m, β-lactam protons), 5.92 (1H,s, α-proton), 6.8 - 7.7 (8H,m, aromatic protons), 8.30 (1H,s, pyrimidine proton).

I claim:

1. A penicillin of formula (I) or a pharmaceutically acceptable non-toxic salt or conventional penicillin in vivo hydrolysable ester thereof:

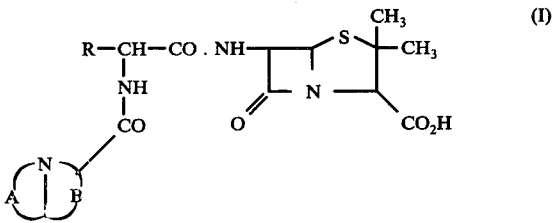

wherein R represents furyl, thienyl, cycloalkyl of up to 6 carbon atoms in the alkyl part, cycloalkenyl of up to 6 carbon atoms in the alkenyl part or phenyl, or phenyl substituted by hydroxy, halogen, nitro, lower alkyl, lower alkoxy, amino, or carboxy; and A and B are the same or different and each represents the residue of a fused 5- or 6-membered ring.

2. A penicillin as claimed in claim 1, having the formula:

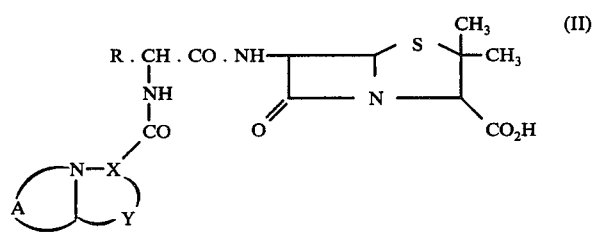

wherein R and A are as defined in claim 1; X represents a group of formula

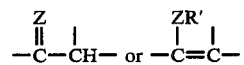

in which Z represents oxygen or sulphur; R' represents hydrogen, lower alkyl or lower alkoxycarbonyl; Y represents the residue of a fused 5- or 6-membered saturated or unsaturated ring.

3. A penicillin as claimed in claim 2 wherein Y is:

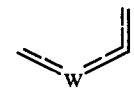

wherein the dotted lines represent optional double bonds in one or two of the positions shown; and when one bond from the group W is a double bond, then W is a nitrogen atom or a —CH— group, and when both bonds from the group W are single bonds then W is an oxygen or sulphur atom or a CH$_2$ or NR$^2$ group wherein R$^2$ is hydrogen or lower alkyl.

4. A penicillin as claimed in claim 3 wherein W is nitrogen or sulphur.

5. A penicillin as claimed in claim 4 wherein W is nitrogen.

6. A penicillin as claimed in claim 2 wherein Z is oxygen.

7. A penicillin as claimed in claim 2 wherein R' is hydrogen.

8. A penicillin as claimed in claim 1 wherein A completes a 5- or 6-membered ring containing from one to four nitrogen atoms and from zero to two sulphur atoms.

9. A penicillin as claimed in claim 8 wherein the radical A completes a pyrazine, pyridine, thiazoline, triazine, thiazolidine, tetrahydropyridine, or tetrazole ring.

10. A penicillin as claimed in claim 1 wherein A completes a 5-membered ring.

11. A penicillin as claimed in claim 10 wherein A completes a pyrazine ring.

12. A penicillin as claimed in claim 1 wherein R is phenyl or 4-hydroxyphenyl.

13. A pharmaceutical composition having antibacterial activity comprising an antibacterially effective amount of a compound as claimed in claim 1 together with a pharmaceutically acceptable carrier.

14. The compound of claim 1 which is 6-D-[2(4-oxo-4H-pyrido[1,2-a]pyrimidine-3-carboxamido)-2-phenylacetamido]-penicillanic acid.

15. The compound of claim 1 which is 6-D-[2-(4,7-dihydro-4-ethyl-7-oxo-pyrazolo[1,5-a]pyrimidine-6-carboxamido)-2-phenylacetamido]penicillanic acid.

16. The compound of claim 1 which is 6-D-[2-(7-hydroxypyrazolo[1,5-a]pyrimidine-6-carboxamido)-2-phenylacetamido]penicillanic acid.

17. The compound of claim 1 which is 6-D-[2-(5-oxo-5H-thiazolo[3,2-a]pyrimidine-6-carboxamido)-2-phenylacetamido]-penicillanic acid.

18. The compound of claim 1 which is 6-D-[2-(7-hydroxy-1,2,4-triazolo[1,5-a]pyrimidine-6-carboxamido)-2-phenylacetamido]penicillanic acid.

19. The compound of claim 1 which is 6-D-[2-(4,7-dihydro-4-ethyl-7-oxo-pyrazolo[1,5-a]pyrimidine-6-carboxamido)-2-p-hydroxyphenylacetamido]penicillanic acid.

20. The compound of claim 1 which is 6-D-[2-(7-hydroxyl-1,2,4-triazolo[1,5-a]pyrimidine-6-carboxamido)-2-p-hydroxyphenylacetamido]penicillanic acid.

21. The compound of claim 1 which is 6-D-[2-(5-oxo-5H-thiazolo[3,2-a]pyrimidine-6-carboxamido)-2-p-hydroxyphenylacetamido]penicillanic acid.

22. The compound of claim 1 which is 6-D-[2-(7-hydroxypyrazolo[1,5-a]pyrimidine-6-carboxamido)-2-hydroxyphenylacetamido]penicillanic acid.

23. The compound of claim 1 which is D-α-(8-methoxy-4-oxo-4H-pyrimido[2,1-b]benzothiazol-3-carbonylamino)benzylpenicillin.

24. The compound of claim 1 which is D-α-(5-oxo-5H-thiazolidino[3,2-a]pyrimidin-6-carbonylamino)-benzylpenicillin.

25. The compound of claim 1 which is D-α-(5-oxo-5H-thiazolidino[3,2-a]pyrimidin-6-carbonylamino)-p-hydroxybenzylpenicillin.

26. The compound of claim 1 which is D-α-(8-methoxy-4-oxo-4H-pyrimido[2,1-b]penzothiazol-3-carbonylamino)-p-hydroxybenzylpenicillin.

27. The compound of claim 1 which is 6-(R-2-(6,7,8,9-tetrahydro-4-oxo-4-H-pyrido[1,2-a]pyrimidine-3-carboxamido)-2-phenylacetamido)penicillanic acid.

28. The compound of claim 1 which is D-α-(7-oxo-7H-1,2,4-triazolo[5,1-b[1,3]thiazine-6-carbonylamino]-benzylpenicillin.

29. The compound of claim 1 which is D-α-(3,7-dihydro-3-amino-2-methyl-7-oxo-s-triazolo[1,5-a]pyridimine-6-carbonylamino)benzylpenicillin.

30. The compound of claim 1 which is D-α-(4,7-dihydro-4-ethyl-7-oxo-1,2,4-triazolo[1,5-a]pyrimidine-6-carbonylamino)p-hydroxybenzylpenicillin.

31. The compound of claim 1 which is D-α-(7-hydroxytetrazolo[1,5-a]pyrididine-3-carbonyl-amino)-benzylpenicillin.

32. The compound of claim 1 which is D-α-(4-oxo-4H-pyrido[2,1-c]as-triazine-3-carbonylamino)benzylpenicillin.

33. The compound of claim 1 which is D-α-(7-chloro-4-oxo-4H-pyrimido[2,1-b]benzoazole-3-carbonylamino)benzylpenicillin.

* * * * *